United States Patent [19]

Barton et al.

[11] 4,220,588

[45] Sep. 2, 1980

[54] CHEMICAL PROCESSES

[76] Inventors: Derek H. R. Barton; David J. Lester, both of Institute de Chimie des Substances Naturelles, 91190 Gif sur Yvette, France; Steven V. Ley, Imperial College, London, England, SW7 2AY

[21] Appl. No.: 8,074

[22] Filed: Jan. 31, 1979

[30] Foreign Application Priority Data

May 31, 1978 [GB] United Kingdom ............... 26114/78

[51] Int. Cl.$^2$ .............................................. C07J 9/00
[52] U.S. Cl. ........................ 260/239.55 A; 260/397.2
[58] Field of Search ................... 260/239.55 A, 397.2, 260/677, 666

[56] References Cited

PUBLICATIONS

Barton et al. I, (1978), J. Chem. Soc. Chemical Comm. pp. 130 and 131.
Barton et al. II, (1978), J. Chem. Soc. Chem., pp. 276 and 277.
Barton et al. III, (1978), J. Chem. Soc. Chem., pp. 952–954.
"Steroids", by Fieser et al. p. 250.

Primary Examiner—Elbert L. Roberts
Attorney, Agent, or Firm—Bacon & Thomas

[57] ABSTRACT $\alpha,\beta$-Unsaturated aldehydes and ketones are prepared by reaction of an arylseleninic anhydride with an aldehyde or ketone having at least one hydrogen atom in the $\alpha$-position which is or can be in the syn-configuration with respect to at least one hydrogen atom in the said $\beta$-position. The ketones used as starting material especially include perhydrophenanthrene ketones such as steroid ketones and the arylseleninic anhydride used may for example be benzeneseleninic anhydride.

16 Claims, No Drawings

CHEMICAL PROCESSES

The present invention relates to processes for the preparation of α,β-unsaturated aldehydes or ketones, particularly in the perhydrophenanthrene series.

Although cycloaliphatic aldehydes and ketones such as steroid ketones may be dehydrogenated by a variety of methods, including the use of selenium dioxide, the known methods have disadvantages and improved techniques are needed. In particular it is desirable to achieve as high a yield of the dehydrogenated product as possible whilst avoiding the disadvantages inherent in handling reagents such as, selenium dioxide which is highly toxic and tends to leave deposits of metallic selenium in the products.

The present invention is based on the discovery that α,β-unsaturated aledhydes and ketones may be prepared by reaction of an arylseleninic anhydride with an aldehyde or ketone having at least one hydrogen atom in the α-position which is or can be in the syn-configuration with respect to at least one hydrogen atom in the said β-position.

It appears that the reagent introduces an arylseleninyl group at the α-position of the steroid which readily eliminates with a syn-hydrogen atom at the β-position to yield the desired α,β-unsaturated aldehyde or ketone.

The syn-elimination according to the invention requires that the hydrogen atom on the β-carbon can come into the syn configuration relative to the aryl selininyl group. Where a cycloaliphatic ketone such as a steroid ketone is concerned it will be appreciated that prevention of bond rotation means that only one of the two substituents on the β-carbon atom can be syn- to the α-seleninyl group and that in such compounds there must be a hydrogen atom on the β-carbon atom which is syn to the α-seleninyl group.

As indicated above, the ketones used as starting material are preferably cycloaliphatic ketones, more particularly perhydrophenanthrene ketones.

It will be appreciated that perhydrophenanthrene aldehydes and ketones for use in the present invention include not only compounds possessing the cyclopentanoperhydrophenanthrene system as in steroid compounds such as steroids of the cholestane, pregnane, androstane, spirostane or lanostane series but also, for example non-steroid perhydrophenanthrene aldehydes and ketones in which, for example the cyclopentane ring of a steroid has been replaced by a cyclohexane, heptahydroindane or decalin ring system which may, if desired, carry substituents such as alkyl groups e.g. methyl groups (as examplified by compounds of the α- or β- amyrin series e.g. α-amyrone or β-amyrone) or isopropenyl groups (as exemplified by compounds of the lupeol series e.g. lupeone).

The keto group of the above-mentioned ketones is preferably present in the A- or C-ring only of the perhydrophenanthrene ketone, for example in the 3- or 12- position, but may, of course be present at any other position on the system e.g. at the 17- or 20- position of steroids.

The steroid ketones for use in the present invention may, for example contain various substituents e.g. alkyl groups such as methyl or ethyl groups in any of the 2-, 4-, 6-, 10, 13-, 14- and 16- positions; a double bond at the 4, 5-, 5,6-, 6, 7-, 12- or 8(9) position; a ketal or orthoester group at the 20- position; hydroxy or protected hydroxy and/or saturated or unsaturated, substituted or unsubstituted hydrocarbon (including acyl e.g. acyloxyacetyl) group at the 17- position; a protected or unprotected hydroxy group at the 11-, 12-, 16-, 17- or 20- position; protected or unprotected hydroxy group at the 21- position; or a halogen atom, e.g. a fluorine or chlorine atom, in the 16-, 11- , 9- or 6- position.

In such substituents, alkyl groups preferably have 1–5 carbon atoms as in methyl or ethyl groups. Protected hydroxy groups may be ether groups (e.g. $C_{1-5}$ alkoxy groups such as methyl or ethyl, or trihydrocarbyl-silyl groups such as trimethylsilyl) or acyloxy groups which preferably have up to 10 carbon atoms, e.g. aroyl groups such as benzoyl or alkanoyl groups such as acetyl.

In general, hydroxy groups are preferably protected during the reaction unless they are relatively inert to the arylseleninyl anhydride reagent Ketal groups preferably have 1–6 carbon atoms e.g. ethylene ketal groups and orthoester groups preferably have 1–6 carbon atoms e.g. orthoacetyl groups.

Substituents at the 17-position include for example the α-hydroxy and β-hydroxyacetyl groups and their ester and ketal derivatives and side chains characteristic of of vitamins of the D-series.

The non-steroid perhydrophenanthrene ketones may, of course, be similarly substituted at corresponding positions on the perhydrophenanthrene ring system where appropriate.

The α-aryl seleninyl- group may be represented by the formula

in which Ar is an aryl group which is preferably a phenyl group or a substituted phenyl group especially a nitrophenyl group e.g. a p-nitrophenyl group.

A starting ketone may possess hydrogen atoms in the α- and β- positions on both sides of the keto group as, for example, in a ring A saturated 3-ketosteroid. Such a ketone may undergo reaction according to the present invention in both α,β-positions to produce a dienone. Thus, for example, cholestan-3-one may be converted into cholesta-1,4-dien-3-one. Where such additional dehydrogenation is required, the quantity of arylseleninic anhydride reagent should be appropriately increased e.g. to 2 equivalents.

The reaction of the aldehyde or ketone with the seleninic anhydride is conveniently effected in the presence of an appropriate solvent, for example, chlorobenzene and advantageously effected at an elevated temperature preferably from 80° C. to the boiling temperature of the reaction mixture e.g. from 95° C. to the boiling temperature of the reaction mixture. The reaction is preferably effected using 0.75 to 1.5 equivalents preferably about 1 equivalent, of the anhydride per equivalent of the aldehyde or ketone. It will be appreciated that where more than one free aldehyde or keto group is present in the starting ketone and the respective α- and β- positions carry hydrogen atoms the preferred equivalent range for the use of selenenic anhydride per equivalent of aldehyde or ketone is multiplied by the number of keto groups in the ketone capable of allowing such production. Alternatively, where only one of such α,β- positions is required to be dehydrogenated, it may be necessary to protect the remaining aldehydes or keto groups selectively.

The arylseleninic anhydride reagent may be formed in situ e. g. from arylseleninic acid under the reaction conditions, for example at temperatures above about 80° C. and it may be convenient to add the acid to the reaction mixture rather than the anhydride.

We have found that reaction times of less than 4 hours are preferred. Where the reaction is allowed to proceed for longer reaction times, for example about 17 or 18 hours, especially where more than 1 equivalent of the anhydride is used, other products can be isolated such as phenylselenated species and/or nor-ketones lacking the α-carbon atom of the α,β-unsaturated ketone.

Indeed, the process of the present invention may also be employed to prepare nor-ketones particularly in the perhydrophenanthrenes by permitting an initially produced α,β-unsaturated ketone to react further with the arylseleninic anhydride reagent. Such a process is, of course, preferably effected by the use of an excess of the arylseleninic anhydride and long reaction times e.g. greater than 10 hours are advantageously used. In particular a 3-keto perhydrophenanthrene can be oxidised in this way to a corresponding A-nor-compound.

The α,β-unsaturated ketone or the nor-ketone may, if desired, be separated from the reaction mixture by any convenient method, for example by preparative layer chromatography. A major by-product of the process for the preparation of the α,β-unsaturated aldehyde or ketone is the corresponding diaryl selenide which can be easily separated from the reaction mixture and, if desired, reoxidised to give the anhydride.

One advantage inherent in the use of an arylseleninic anhydride instead of selenium dioxide is that the anhydride is relatively unreactive towards the ethylenic linkage in contrast to selenium dioxide and does not oxidise CHO groups.

In general, α,β-unsaturated aldehydes and ketones are of great importance in synthetic organic chemistry and in particular in the perhydrophenanthrenes. Thus, for example, 3-oxo steroids having double bonds in the 1- and/or 4-positions are prominent among the antiinflammatory and progestational drugs and 12-oxo steroids having a 9(11)-double bond are important in the synthesis of corticoids. Steriod 3-keto 1,4,6-trienes are important in the synthesis of 1α-hydroxyvitamin $D_3$ and its analogues.

The following Examples illustrate the present invention:

EXAMPLE 1

Preparation of cholesta-1,4-dien-3-one by reaction of cholestan-3-one with Benzeneseleninic Anhydride (B.S.A.)

Cholestan-3-one (100 mg) was dissolved in chlorobenzene (5 ml), benzeneseleninic anhydride (188 mg, 2 equiv.) added and the solution heated to reflux with stirring under nitrogen in the dark. After 3 hours tlc showed almost complete reaction. The mixture was allowed to cool before filtering down a short silica column, washing with petrol containing 10% methylene chloride followed by releasing the crude product by washing with methanol. On evaporation an oil (107.1 mg) was obtained which crystallised on cooling in card-ice. mp. 50°–57° C. Plc of the resulting impure product yielded 63.3 mg (63%) of cholesta-1,4-dien-3-one mp. 110°–112° C. (literature melting point 112° C.). $\lambda_{max}$.242 nm ($\epsilon$ 14500) (literature U.V. absorption 242 nm ($\epsilon$ 15000)). I.R. spectrum identical to previously prepared pure samples. The results of several runs are tabulated below:

| BSA (moles) | Time (hours) | Yield of dienone (%) |
|---|---|---|
| 1 | 3 | 50 |
| 2 | 3 | 76 |
| 3 | 18 | 69* |

*No cholesta-1,4,6-trien-3-one was detected

EXAMPLE 2

Preparation of cholesta-1,4-dien-3-one by reaction of cholest-1-en-3-one with Benzeneseleninic Anhydride Cholest-1-en-3-one (40 mg) was dissolved in chlorobenzene (0.5 ml), benzeneseleninic anhydride (38 mg, 1 equiv) added and the stirred mixture heated to 95° C. under nitrogen. Reaction was followed by tlc and appeared complete after only 45 minutes. Plc ($CH_2Cl_2$) gave the product the title in 76% yield m.p. 109°–111° C. (literature m.p. 112° C.).

EXAMPLE 3

Preparation of cholesta-1,4,6-trien-3-one by reaction of cholesta-4,6-dien-3-one with Benzeneseleninic Anhydride Cholesta-4,6-dien-3-one (50 mg) was dissolved in chlorobenzene (0.5 ml), benzeneseleninic anhydride (48 mg, 1 equiv,) added and the stirred mixture heated to 95° C. Plc showed complete reaction after 55 min, this was confirmed by U.V. control. Plc afforded the product of the title as an oil (42 mg) which could be recrystallised from methanol. U.V. spectra on the oil showed the product of the title to be present in 66% yield.

EXAMPLE 4

Reaction of Lanostan-3-one with Benzeneseleninic Anhydride

Lanostan-3-one (100 mg.) was dissolved in chlorobenzene (0.7 ml.) benzeneseleninic anhydride added (85 mg., 1 m. equiv.) and the stirred mixture heated to 95° C. under purified nitrogen. Reaction was followed by both tlc and I.R. A band at 1670 cm$^{-1}$ appeared and the band at 1700 cm$^{-1}$ disappeared. A further new band was also observed from the start of the reaction. The reaction was complete after 45 minutes and the reaction mixture was subjected to plc which yielded in order of increasing polarity, diphenyl diselinide; A band (5.0 mg) resolvable into two components on Merck active plates, one component was identical to authenic 2-phenyl-selenated lanostan-3-one $\nu_{max}$. 1700 cm$^{-1}$ 1665 cm$^{-1}$ (contaminant); a faint red band (12.3 mg, 13%) m.p. 98°–100° C., $\nu_{max}$. 1745 cm$^{-1}$, nmr signals only in the range 1.6–0.7 $[\alpha]_D^{22}$ 206° (c. 0.050), thus shown to be the A-nor compound: and the major product Lanosta-1-en-3-one (67.0 mg, 67% recrystallised as needles from ethanol) m.p. 119°–120° C. (literature m.p. 118°–120° C.), $\nu_{max}$. 1670 cm$^{-1}$, $\lambda_{max}$ 232 n.m. ($\epsilon$ 9200) (literature $\lambda_{max}$. 229 n.m. ($\epsilon$ 9000)) M+ 426, $[\alpha]_D^{22}$ =48.4° (c 0.100) (literature $[\alpha]_D$+47° (c 0.53)).

The results of several other runs are summarised in Table I in which

"BSA" is benzeneseleninic anhydride;
"1-enone" is lanosta-1-en-3-one;
"A-nor" is A-norlanostanone;
"2-PhSe" is 2-phenylselenated lanostan-3-one; and "N.I." means "not isolated"

TABLE I

| BSA (eqv.) | 1-enone (%) | A-nor (%) | 2-PhSe (%) | Time | Comments |
|---|---|---|---|---|---|
| 1 | 63 | NI | NI | 20 m | Contaminated with A-nor compound. |
| ⅔ | 84 | NI | NI | 20 m | Contaminated with both A-nor compound and starting material. Not possible to purify by crystallisation. |
| ⅔ | 74 | NI | 8 | 25 m | Phenylselenated band resolvable into two components on active tlc plates. |
| 2 | 66 | 17 | NI | 105 m | |
| 1 | 71 | 17 | NI | 1 h | |
| 2 | 40 | 39 | 0 | 18 h | Several polar bands not isolated. |
| 1 | 67 | 13 | 4 | 45 m | 1-enone pure and completely free of all above contaminants. Other more polar products observed on plc but not isolated. |

EXAMPLE 5

Reaction of 4,4-dimethylcholest-5-en-3-one with Benzeneseleninic Anhydride 4,4-Dimethylcholest-5-en-3-one (100 mg.) was dissolved in chlorobenzene (0.7 ml.), BSA (87 mg., 1 m. equiv.) added and the stirred mixture heated to 95°–100° C. under purified nitrogen. The reaction was followed by I.R. spectroscopy as before. Complete reaction was observed after 35 minutes and the mixture subjected to plc. Each band could easily be recrystallised from ethanol or ethanol/water as necessary. The following were isolated; Diphenyl diselenide, Least polar, 47.7 mg. (63%), a faint pink band later shown to be the A-nor compound (see next Example) and 4,4-dimethylcholest-1,5-dien-3-one (71.1 mg crude, 67% recrystallised) as fine needles m.p. 75°–6° C. (literature m.p. 77°–78° C.) $\nu_{max}$. 1685 cm$^{-1}$., $\lambda_{max}$. 230 ($\epsilon$ 7200)) (literature U.V. absorption 227 nm (68 9350)), 6.6. (1H,d), 5.9 (1H,d), 5.6 (1H, m), M+· 410, $[\alpha]_D^{22}$ 54.9° (c 0.100) (literature $[\alpha]_D$ 53° (c 1.00)).

EXAMPLE 6

Reaction of 4,4-dimethylcholest-5-en-3-one with excess Benzeneseleninic Anhydride 4,4-Dimethylcholest-5-en-3-one (100 mg) was dissolved in chlorobenzene (0.5 ml.), BSA (174 mg, 2 equiv.) added and the stirred mixture heated under purified nitrogen at 95°–100° C. for 17 hours. Plc yielded in order of increasing polarity; diphenyldiselenide 101 mg. 133% based on steroid), A faint pink compound characterised as the A nor compound (26.7 mg., 28% recrystallised from ethanol/water) m.p. 127°–128° C. (literature m.p. 129°–130° C.)$\nu_{max}$. 1745 cm$^{-1}$ $\lambda_{max}^{CHCl_3}$ 304 nm ($\epsilon$ 70) (literature U.V. absorption $\lambda_{max}$. 300 nm ($\epsilon$ 94)) δ2.1 (2 H, m), 5.6 (1 H) (literature, 2.15 (2 H), 5.4 (1 H)) $[\alpha]_D^{22}$ +53° (c 0.100) (literature $[\alpha]_D$ +54.5° (c. 26)); and 4,4-dimethylcholest-1,5-dien-3-one (30.7 mg, from ethanol, 31%) identical with previous samples. The plate showed many other more polar decomposition products which were not isolated.

EXAMPLE 7

Reaction of α-Amyrone with Benzeneseleninic Anhydride

α-Amyrone (100 mg) was dissolved in chlorobenzene (0.7 ml) BSA (85 mg, 1 mole equiv.) added and the stirred mixture heated to 95°–100° C. under purified nitrogen. The reaction was followed by I.R. spectroscopy and completion of the reaction was observed after 25 minutes. The mixture was subjected to plc to yield diphenyldiselenide (54.9 mg., 75%), a faint red band later shown to be the nor compound and α-amyr-1-enone (74.0 mg., 74%) as a white crystalline solid m.p. 156°–158° C., $\nu_{max}$. 1665 cm$^{-1}$, $\lambda_{max}$. 229 nm. ($\epsilon$ 8800) M+· 422, $[\alpha]_D^{22}$ 136.4°. (c 1.00).

EXAMPLE 8

Reaction of α-Amyrone with excess Benzeneseleninic Anhydride

α-Amyrone (100 mg) was dissolved in chlorobenzene (0.5 ml.). benzeneseleninic anhydride (170 mg. 2 mole equiv.) added and the mixture heated to 95°–100° C. with stirring under nitrogen for 17 hours. Plc yielded diphenyldiselenide (104 mg., 140% based on steroid), the A-nor compound (46.3 mg. as an oil, 37 mg. crystalline from ethanol, 39%) m.p. 189°–191° C., $\nu_{max}$. 1745 cm$^{-1}$, $[\alpha]_D^{22}$ 440° (c 0.050) and α-amyr-1-enone (38.8 mg. 39% crystalline) identical with previous sample.

EXAMPLE 9

Reaction of β-Amyrone with Benzeneseleninic Anhydride

β-Amyrone (100 mg.) was dissolved in chlorobenzene (0.5 ml) benzeneseleninic anhydride (85 mg., 1 m. equiv.) added and the stirred mixture heated to 95°–100° C. under purified nitrogen for 15 minutes. Plc yielded diphenyldiselenide (56.3 mg. 76%), material assumed to be phenylselenated material (7.6 mg), the ring A nor compound, identical with the characterised sample (7.3 mg., 9%) and β-amyr-1-enone (54.0 mg, recrystallised from ethanol 54%) m.p. 174°–175° C. (literature m.p. 174°–5° C.), $\lambda_{max}$. 230 nm ($\epsilon$ 8000) literature U.V. absorption $\lambda_{max}$. 230 nm ($\epsilon$ 9700). $\nu_{max}$. 1665 cm$^{-1}$ M+· 422 $[\alpha]_D^{22}$ 140° (c 0.050) (literature $[\alpha]_D$ 141° (c 1.5)).

EXAMPLE 10

Reaction of β-Amyrone with excess Benzeneseleninic Anhydride

β-Amyrone (100 mg.) was dissolved in chlorobenzene (0.5 ml.), benzeneseleninic anhydride (170 mg) added and the mixture heated to 95°–100° C. with stirring under purified nitrogen for 17 hours. Plc yielded diphenyldiselenide (130.7 mg. 178% based on steroid), a faint orange band shown to be the A-nor compound (35 mg, 36% recrystallised from ethanol/water) m.p. 168°–170° $\nu_{max}$. 1745 cm$^{-1}$, $[\alpha]_D^{22}$ 226° (c 0.025) and β-amyr-1-enone (20.3 mg. 21%) identical with previously prepared samples.

EXAMPLE 11

Reaction of Lupenone with Benzeneseleninic Anydride

Lupenone (100 mg) was dissolved in chlorobenzene (0.5 ml.), benzeneseleninic anhydride (85 mg) added and the stirred mixture heated to 95°–100° C. under purified nitrogen. The reaction was complete after 15 minutes and plc yielded diphenyldiselenide (50 mg, 68%) and lup-1-enone (58%) as the major products of the reaction. m.p. 173-4 (literature m.p. 173°-4° C.) $\nu_{max}$. 1665 cm$^{-1}$.

EXAMPLE 12

Reaction of Hecogenin Acetate with Benzeneseleninic Anhydride

Hecogenin acetate (100 mg) was dissolved in chlorobenzene (1 ml.), benzeneseleninic anhydride (152 mg. 2 equiv.) added and the stirred mixture heated to reflux under purified nitrogen. The reaction was followed by I.R., observing the complete disappearance of the band at 1700 cm$^{-1}$. After 50 minutes, the reaction appeared complete by I.R. control. On cooling a white precipitate of unreacted anhydride formed. The complete mixture was washed down a silica column using 10% methylene chloride in petrol to remove most of the diphenyldiselenide. Washing with methanol afforded, after evaporation, the reaction products as white needles. (166.7 mg.). Plc (methylene chloride containing 7% methanol) afforded white needles of the 9(11)-enone of hecogenin acetate (90.3 mg 91%). m.p. 217°-220° C. (literature m.p. 218°-220° C.) $\lambda_{max}$. 237 nm ($\epsilon$ 1900) (literature U.V. absorption 238 nm ($\epsilon$ 1500) $[\alpha]_D^{20}$ −7.6° (c 0.100) (literature $[\alpha]_D^{20}$ −8.7°).

EXAMPLE 13

Preparation of $\Delta^{1,4,6}$-cholestatrien-3-one $\Delta^{4,6}$-cholestadien-3-one (10.0 g) was dissolved in chlorobenzene (distilled from P$_2$O$_5$, 80 ml) and the stirred solution heated to 95° C. under nitrogen in the dark. Benzeneseleninic anhydride (10.0 g) was added in portions to the stirred mixture over a period of 1 hour. The anhydride dissolved and the reaction mixture acquired a deep yellow colour. After 1 hour the mixture was set aside in the fridge to crystallise (1–2 hours). The crystalline phenylseleninic acid (4.6 g) was filtered, and washed with a little cold chlorobenzene. The filtrate was distilled under reduced pressure to remove the chlorobenzene, care being taken to ensure that the temperature did not rise above 90° C. The $\Delta^{1,4,6}$-cholestatrien-3-one was obtained in the form of a yellow oil and was characterised by conversion to the 1, 2$\alpha$-epoxide by dissolving in methanol (250 ml) at room temperature, adding methanolic sodium hydroxide (10%, 2.6 ml) and hydrogen peroxide (30 vol, 18 ml) to the mixture and allowing the mixture to stand at room temperature overnight. On cooling in cardice/acetone, an almost colourless solid was obtained which was filtered at the pump. Yield 6.0 g m.p. 91°-4° C. $[\alpha]^{22}$ 96° (c. 04). The filtrate was treated with metabisulphite followed by ether extraction and column chromatography to yield diphenyldiselenide as a standard recovery procedure.

The crude product was recrystallised from methanol as colourless needles (5.5 g) m.p. 96°-8° C. $[\alpha]_D$ 168° (c. 07).

Recrystallisation from methanol/acetone resulted in the title product having literature m.p. and rotation although recovery was not good (ca 55–60%).

EXAMPLE 14

Reaction of benzeneseleninic acid with hecogenin acetate

To a solution of hecogenin acetate (100 mg; 0.21 m.mole) in dry chlorobenzene (1 ml) was added benzeneseleninic acid (77 mg.; 0.42 m.mole) and the solution heated to 110° C. with stirring under nitrogen for 160 minutes. P.L.C. afforded 9(11)-dehydrohecogenin acetate (80.8 mg.; 81%) m.p. 217°-220° C. Identical with authentic material.

EXAMPLE 15

Reaction of benzeneseleninic acid with lanostanone

To a solution of lanostanone (100 mg.; 0.23 m.mole) in dry chlorobenzene (1 ml) was added benzeneseleninic acid (85 mg.; 0.46 m.mole) and the solution heated to 110° C. with stirring under nitrogen for 150 minutes. P.L.C. afforded lanost-1-enone (63.5 mg.; 64%) m.p. 119°-120° C. (from methanol) and A-nor-lanostanone (9.4 mg.; 10%) both products identical with authentic materials.

We claim:

1. A process for the preparation of an $\alpha,\beta$-unsaturated aldehyde or ketone which comprises reacting an arylseleninic anhydride having the formula

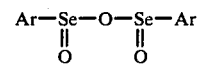

in which Ar represents an unsubstituted phenyl or nitrophenyl with a cycloaliphatic aldehyde or ketone having at least one hydrogen atom in the $\alpha$-position which is or can be in the synconfiguration with respect to at least one hydrogen atom in the said $\beta$-position.

2. A process as claimed in claim 1 wherein the aldehyde or ketone used is a perhydrophenanthrene ketone.

3. A process as claimed in claim 2 wherein the perhydrophenanthrene ketone used is a steroid ketone.

4. A process as claimed in claim 3 wherein the steroid ketone used is of the cholestane, lanostane, pregnane, androstane or spirostane series.

5. A process as claimed in claim 2 wherein the perhydrophenanthrene ketone used has the ring system of a steroid in which the cyclopentane ring thereof has been replaced by a cyclohexane, heptahydroindane or decalin ring(s).

6. A process as claimed in claim 5 wherein the perhydrophenanthrene ketone used is of the $\alpha$-amyrin, $\beta$-amyrin or lupeol series.

7. A process as claimed in claim 2 wherein the perhydrophenanthrene ketone used has a keto group present in the A or C ring only.

8. A process as claimed in claim 2 wherein the perhydrophenanthrene ketone used carries an alkyl group in any of the 2-, 4-, 6-, 10-, 13- and/or 14-positions; a double bond at the 4,5-, 5,6-, 6,7-, 8,9 and/or 12,13 positions; a protected hydroxy group at the 11- or 12-position; and/or a halogen atom at the 11-, 9- and/or 6-position.

9. A process as claimed in claim 2 wherein the perhydrophenanthrene ketone used is a steroidal ketone which may carry an alkyl group in the 16-position; a ketal or orthoester group at the 20-position; a hydroxy, acyloxy or alkoxy and/or hydrocarbon group at the 17-position; a hydroxy group at the 16-, 17- or 20-position; an esterified hydroxy group at the 21-position; and/or a halogen atom at the 16-position.

10. A process as claimed in claim 1 wherein from 0.75 to 1.5 equivalents of seleninic anhydride is used per double bond to be introduced.

11. A process as claimed in claim 10 wherein about 1 equivalent of seleninic anhydride is used per double bond to be introduced.

12. A process as claimed in claim 1 wherein the reaction is effected at an elevated temperature.

13. A process as claimed in claim 12 wherein the reaction is effected at a temperature of from 80° C. to the boiling temperature of the reaction mixture.

14. A process as claimed in claim 1 wherein the reaction is effected in the presence of chlorobenzene as solvent.

15. A process as claimed in claim 5 wherein said cyclohexane, heptahydroindane or decalin ring(s) carry one or more alkyl substituents.

16. A process as claimed in claim 1, wherein Ar represents p-nitrophenyl.

* * * * *